(12) United States Patent
Karakaya et al.

(10) Patent No.: US 11,389,062 B2
(45) Date of Patent: Jul. 19, 2022

(54) SYSTEM AND METHOD FOR DETERMINING A RISK LEVEL OF A RESPIRATORY ATTACK

(71) Applicant: KONINKLIJKE PHILIPS N.V., Eindhoven (NL)

(72) Inventors: Koray Karakaya, Eindhoven (NL); Ronaldus Maria Aarts, Geldrop (NL); Maarten Petrus Joseph Kuenen, Veldhoven (NL); Kiran Hamilton J. Dellimore, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 989 days.

(21) Appl. No.: 16/079,576

(22) PCT Filed: Feb. 28, 2017

(86) PCT No.: PCT/EP2017/054538
§ 371 (c)(1),
(2) Date: Aug. 24, 2018

(87) PCT Pub. No.: WO2017/148876
PCT Pub. Date: Sep. 8, 2017

(65) Prior Publication Data
US 2021/0183518 A1    Jun. 17, 2021

(30) Foreign Application Priority Data
Mar. 1, 2016  (EP) .................................... 16157989

(51) Int. Cl.
*A61B 5/00*  (2006.01)
*G16H 50/80*  (2018.01)
(Continued)

(52) U.S. Cl.
CPC .......... *A61B 5/0022* (2013.01); *A61B 5/0816* (2013.01); *A61B 5/091* (2013.01);
(Continued)

(58) Field of Classification Search
CPC ..... A61B 5/0022; A61B 5/0816; A61B 5/091; A61B 5/1112; A61B 5/1118;
(Continued)

(56) References Cited

U.S. PATENT DOCUMENTS 6,231,519 B1 * 5/2001 Blants .................... A61B 5/411
600/529
6,288,646 B1    9/2001 Skardon
(Continued)

FOREIGN PATENT DOCUMENTS

WO    2016193049 A1    12/2016

OTHER PUBLICATIONS

Seto, Edmund Y.W. et al., "A wireless body sensor network for the prevention and management of asthma", Industrial Embedded Systems, 2009. SIES '09. IEEE International Symposium on Jul. 2009.
(Continued)

*Primary Examiner* — Omar Casillashernandez

(57) ABSTRACT

A system determines a risk level of a respiratory attack of a user of the system. The system comprises part of a network of systems, and it reports information to, and receives information from, the network. The system comprises a local activity monitoring device for tracking the physical activity level of the user. Location information and activity levels in respect of other users of the network of systems are received, relating to when they have suffered a respiratory attack. A warning can then be given to the user which takes account of the location of the user and the activity level or planned activity level of the user, and the received location information and activity levels in respect of other users.

15 Claims, 3 Drawing Sheets

(51) Int. Cl.
*G16H 40/63* (2018.01)
*G16H 40/67* (2018.01)
*G16H 50/30* (2018.01)
*A61B 5/08* (2006.01)
*A61B 5/091* (2006.01)
*A61B 5/11* (2006.01)
*H04L 67/125* (2022.01)
*H04L 67/50* (2022.01)

(52) U.S. Cl.
CPC ........... *A61B 5/1112* (2013.01); *A61B 5/1118* (2013.01); *A61B 5/7275* (2013.01); *A61B 5/746* (2013.01); *A61B 5/7475* (2013.01); *G16H 40/63* (2018.01); *G16H 40/67* (2018.01); *G16H 50/30* (2018.01); *G16H 50/80* (2018.01); *H04L 67/125* (2013.01); *H04L 67/22* (2013.01); *A61B 2560/0242* (2013.01); *A61B 2562/0219* (2013.01)

(58) Field of Classification Search
CPC ..... A61B 5/7275; A61B 5/746; A61B 5/7475; A61B 2560/0242; A61B 2562/0219; A61B 5/0826; A61B 5/411; A61B 5/0008; A61B 5/6898; G16H 40/67; G16H 50/30; G16H 40/63; G16H 50/80; H04L 67/125; H04L 67/22
USPC ........................................................ 340/511
See application file for complete search history.

(56) References Cited

U.S. PATENT DOCUMENTS

| | | | | |
|---|---|---|---|---|
| 9,368,014 | B1* | 6/2016 | Bittman | ................. G16H 40/63 |
| 2002/0186137 | A1 | 12/2002 | Skardon | |
| 2009/0149153 | A1* | 6/2009 | Lee | ................... H04M 1/72424 455/404.1 |
| 2010/0137733 | A1 | 6/2010 | Wang et al. | |
| 2012/0130201 | A1 | 5/2012 | Jain | |
| 2014/0142456 | A1 | 5/2014 | Fischer et al. | |
| 2014/0213925 | A1* | 7/2014 | Chan | .................... A61B 5/7405 600/538 |
| 2014/0229200 | A1 | 8/2014 | Chan et al. | |
| 2015/0174349 | A1 | 6/2015 | Tunnell et al. | |
| 2016/0007913 | A1 | 1/2016 | Darket | |

OTHER PUBLICATIONS

Morreale, Patricia. "Wireless sensor network applications in urban telehealth", Advanced Information Networking and Applications Workshops, 2007, AINAW'07. 21st International Conference on. vol. 2. IEEE, 2007.
Wang, Dong, et al. "Using humans as sensors: An estimation-theoretic perspective." Proceedings of the 13th international symposium on Information processing in sensor networks. IEEE Press, 2014.
Montuschi, Paolo, et al. "Increased 8-isoprostane, a marker of oxidative stress, in exhaled condensate of asthma patients." American journal of respiratory and critical care medicine 160.1 (1999): 216-220.
Zayasu, Kiyoshi, et al. "Increased carbon monoxide in exhaled air of asthmatic patients." American Journal of Respiratory and Critical Care Medicine 156.4 (1997): 1140-1143.
Kharitonov, Sergei A., and Peter J. Barnes. "Exhaled markers of pulmonary disease." American journal of respiratory and critical care medicine 163.7 (2001): 1693-1722.
Oletic, Dinko, Bruno Arsenali, and Vedran Bilas. "Towards continuous wheeze detection body sensor node as a core of asthma monitoring system." Wireless Mobile Communication and Healthcare. Springer Berlin Heidelberg, 2012. 165-172.
Tseng, Vincent S., Chao-Hui Lee, and Jessie Chia-Yu Chen. "An integrated data mining system for patient monitoring with applications on asthma care", Computer-Based Medical Systems, 2008.
Jeong, Hee Young, and Rosa I. Arriaga. "Using an ecological framework to design mobile technologies for pediatric asthma management." Proceedings of the 11th International Conference on Human-Computer Interaction with Mobile Devices and Services. ACM, 2009.
Chu, Hsueh-Ting, et al. "A ubiquitous warning system for asthma-inducement", Sensor Networks, Ubiquitous, and Trustworthy Computing, 2006. IEEE International Conference on. vol. 2. IEEE, 2006.
"Reading the Charts", American Academy of Allergy Asthma & Immunology, Milwaukee, WI, 2018.
Allergie Radar, http://allergieradar.nl/, Accessed 2018.
National Allergy Map, https://www.pollen.com/, Accessed 2018.

* cited by examiner

SYSTEM AND METHOD FOR DETERMINING A RISK LEVEL OF A RESPIRATORY ATTACK

CROSS-REFERENCE TO PRIOR APPLICATIONS

This application is the U.S. National Phase application under 35 U.S.C. § 371 of International Application Serial No. PCT/EP2017/054538, filed on 28 Feb. 2017, which claims the benefit of European Application Serial No. 16157989.1, filed on 1 Mar. 2016. These applications are hereby incorporated by reference herein.

FIELD OF THE INVENTION

This invention relates to a system for warning a user that they are at an increased risk of suffering a respiratory attack, such as an asthma attack, so that preventative measures may be taken. In particular, the invention relates to a system having a network of users, whereby information is shared between users to enable the warning system to be implemented.

BACKGROUND OF THE INVENTION

Sensor networks for facilitating dissemination of local and temporal information for managing and supporting public health are known. Various examples of network-based air quality monitoring and patient tracking systems have been proposed. These approaches have also been applied in the field of managing chronic respiratory track conditions such as asthma.

Detecting asthma triggers and symptoms is a well-studied area. Tracking symptoms and indicators in exhaled breath compounds such as 8-isoprostane, carbon monoxide (CO), and other exhaled breath biomarkers is an approach for managing asthma by means of predicting and preventing asthma attacks. This approach can also extend to monitoring the physical indicators of asthma symptoms, such as tracking wheezing sounds with an on-body acoustic detector e.g. one or more microphones.

A broader approach is to incorporate environmental data as well, such as air quality and allergen/pollen indicators, for providing a better coverage of the patient management system, as well as generating location based advice and warnings.

Thus, various approaches are known for asthma warning systems, including using breath markers, tracking environmental conditions such as allergens/pollens and giving location based advice and sharing user feedback to a networked system.

The type of asthma and the severity reactions to different types of asthma attack triggers depend on the profile of the patient. For example, the type and the concentration of pollens that triggers an asthma attack can be very different from one patient to the other.

Moreover, detecting the asthma attack triggers—for pollens in particular-before they trigger an attack is very difficult for devices that are to be a part of a body area network (e.g. small size, wearable, etc.). One fundamental technical barrier is the amount of air sample that can be processed for capturing the presence and concentration of various types of pollens. A pollen concentration (per air volume) as low as 20 parts/m$^3$ is considered as a high concentration, according to the guidelines of the National Allergy Bureau (NAB). Counting pollen at a statistically meaningful accuracy level requires the processing of large volumes of sample air by the pollen detector, at least comparable to the inhaled air volume during breathing.

Implementation of a reliable pollen identification feature, i.e. with acceptable false positive and false negative indications, for use as a pollen sensor is thus challenging.

US 2014/0229200 discloses a system which monitors a network of users. A user is given a warning of a possible asthma attack based on their own conditions but also based on experiences of other patients with a similar profile. The system may take account of environmental data, the user's altitude, temperature as well as the individual patient's prior history in terms of asthma attacks experienced under particular conditions.

Seto, Edmund Y W, et al. "A wireless body sensor network for the prevention and management of asthma", Industrial Embedded Systems, 2009. SIES '09. IEEE International Symposium on. IEEE, discloses the use of motion sensors for tracking the type of activity and making it a part of an asthma management sensor network.

The trigger is still however based on detecting the allergen concentration as well as the number of events per location. As explained above, a reliable detection of concentration remains challenging to achieve in a wearable device. Moreover, warnings given to other users of an asthma management network/system remain at a generic level. This generates a number of 'false positives' and 'false negatives' for those who do not have the same activity levels as the ones who have triggered the alert.

SUMMARY OF THE INVENTION

The invention is defined by the claims.

According to examples in accordance with an aspect of the invention, there is provided a system for determining a risk level of a respiratory attack of a user of the system, wherein the system comprises part of a network of systems, the system comprising:

an input for receiving information of a physical activity level or a planned physical activity level of the user;

an input for receiving location information of the user;

an input for receiving an indication from the user of a respiratory attack;

an input for receiving location information and activity levels in respect of other users of the network of systems relating to when they have suffered a respiratory attack;

an output for reporting location information and activity level information of the user to other users of the network of systems relating to when the user has suffered a respiratory attack; and a user interface for providing a warning to the user which takes account of the location of the user and the activity level or planned activity level of the user and the received location information and activity levels in respect of other users, wherein the user interface is adapted to provide a warning to the user only if their location and physical activity level or planned physical activity level is comparable to, or higher than, another user that suffered a respiratory attack.

In this system, an activity level and location of a user is monitored, and activity levels and locations at which other system users have suffered an attack are received. In this way, a network of users shares information so that a reliable warning may be given to the user of each system. At the limit, there is only a need to monitor the activity level and location of the user using worn or carried sensors, and this can be achieved with low cost sensors which may for example already be implemented by other devices such as mobile telephones. The dependence of the system on an accurate air quality monitoring system for triggering an alert is minimized.

Even if local air quality monitoring is provided for additional data input, the system is able to provide a warning without any need for this data. Thus, the system has the capability to provide a warning based on activity information without any locally generated particle or other allergen sensing information.

The system thus provides personalized real-time advice for asthma patients. The warning may for example be used as an indicator to avoid physical exercise and/or take antihistamines, thereby leading to a reduced risk levels of respiratory attacks. The system is able to increase the spatial resolution for tracking asthma triggering factors and the chance for successful timely intervention.

The activity monitoring device for example comprises an inertia sensor. This provides a low-cost way to monitor the activity level, and the inertia sensor may be part of another device with which the system communicates.

The system preferably comprises a processor which is adapted to estimate an air volume per breath based on the activity level and on a default air volume per breath for the user.

In this way, a parameter which correlates to the amount of air breathed may be obtained. It combines the normal (i.e. zero activity), breathing volume of the user with their activity level so that an estimate of the breathing characteristics can be made.

The processor may then be adapted to derive a trigger amount based on an estimated total breathed air volume. This total breathed air volume can be derived from the volume per breath and the number of breaths or an estimate of the number of breaths, for example based on a time duration.

By monitoring and/or estimating a total breathed air volume, the (relative) exposure to a pollutant or allergen or other external triggers can be determined. This can be based on the air volume per breath and a time duration. Thus, the attack warning can be based on a determined level of exposure of the user.

This determination of total breathed air volume provides a normalization step. For example a first user with a relatively high activity level may experience an attack. By normalizing this information by considering the high activity level, a location-based alert is not given to others who do not have a high activity. Instead, a warning is only given if they also have a comparably high activity level (or planned activity level) as the first user who has experienced an attack.

The system may further comprise a breathing counter, wherein the breathing counter information is used for estimating the total breathed air volume.

The system may comprise an external input for receiving information about pollution or allergen or other external triggers concentrations at the location of the user.

In this way, the pollution levels can be taken into account based on externally received information, such as public broadcasts of information. These provide location specific pollution information, without the need for local pollution sensing.

The system may comprise an input for receiving information relating to the sensitivity of the user to particular triggers, and wherein the warning takes account of the sensitivity information.

The users may for example be classified into categories depending on their sensitivities, and the information received about other users is then interpreted taking this into account so that a more accurate warning may be given. For example, within a group of users with similar sensitivities, the first one who is going to have an attack will be the one who has the highest activity level.

The input for receiving an indication from the user of a respiratory attack may comprise an emergency button. This provides a simple way for a user to input information to indicate that they have suffered a respiratory attack.

The system may have no local pollution sensing apparatus, or else it may further comprise a pollution sensor for supplementing the generation of the warning.

Examples in accordance with another aspect of the invention provide a method for determining a risk level of a respiratory attack of a user who uses a risk assessment system, wherein the system comprises part of a network of systems, the method comprising:

tracking the physical activity level of the user or determining a planned physical activity level for a user;

receiving an indication from the user if and when they suffer a respiratory attack;

receiving location information and activity levels in respect of other users of the network of systems, relating to when they have suffered a respiratory attack;

reporting location information and activity level information of the user to other users of the network of systems, relating to when the user has suffered a respiratory attack; and providing a warning to the user which takes account of the location of the user and the activity level or planned activity level of the user and the received location information and activity levels in respect of other users, wherein a warning is provided to the user only if their location and physical activity level or planned physical activity level is comparable to, or higher than, another user that suffered a respiratory attack.

The method may comprise estimating an air volume per breath based on the activity level and on a default air volume per breath for the user. A trigger amount may be provided based on an estimated total breathed air volume. Information may also be received about pollution or allergen concentrations at the location of the user. In this way, the pollution levels can be taken into account based on externally received information, such as public broadcasts of information.

Generating the warning may also take account of the sensitivity of the user to particular triggers.

The processing of data may be carried out by a computer program.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a system which determines a risk level of a respiratory attack of a user of the system. The system comprises part of a network of systems, and it reports information to, and receives information from, the network of systems. The system comprises a local activity monitoring device for tracking the physical activity level of the user. Location information and activity levels in respect of other users of the network of systems are received, relating to when they have suffered a respiratory attack. A warning can then be given to the user which takes account of the location of the user and the activity level or planned activity level of the user, and the received location information and activity levels in respect of other users.

Figure 1:
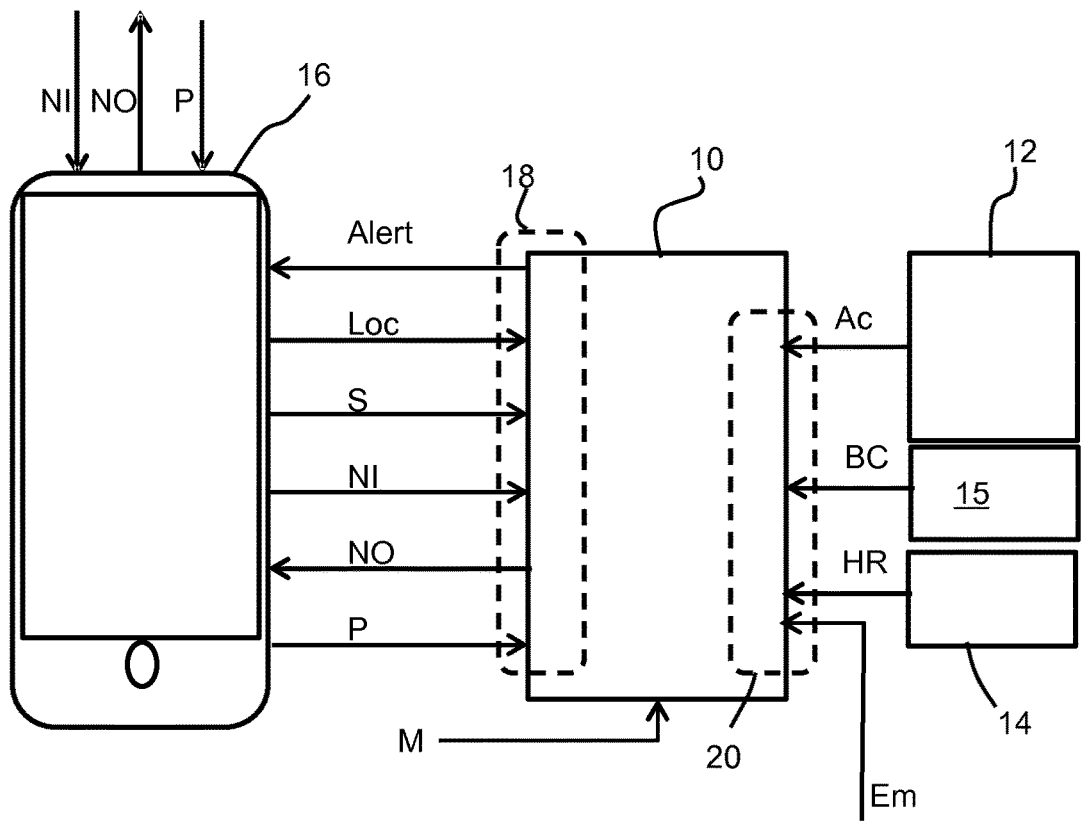
FIG. 1 shows a risk assessment system.

FIG. 1 shows a system of the invention. The system shown is associated with (and carried by) a particular user. There are multiple users each with a similar system, and together they form a network of users and hence a network of systems. The invention will be described in connection with a system for giving warnings about an asthma attack, but respiratory attacks may result from other allergen based conditions, such as any respiratory tract condition that is activated by an external trigger.

The system comprises a processor 10 which receives various inputs in order to generate a warning which is specific to a particular user at a particular location.

The inputs comprise:

a location input "Loc" identifying the current location of the user;

(optionally) a sensitivity input "S" indicating the sensitivity of the user to an asthma attack either generally or in respect of specific allergens;

an activity level input "Ac" for receiving information about the physical activity level of the user;

(optionally) a heart rate input "HR" for tracking the heart rate of the user as an additional source of activity level information, provided by a heart rate monitor 14;

(optionally) a breathing count input "BC" provided by a breathing counter 15;

(optionally) a pollution input "P" for receiving pollution information from external sources, such as external databases;

(optionally) a medication intake input, M, that is coupled to the so-called 'rescue medication' intake, by means of self-reporting and/or using connected medication dispensers (e.g. inhaler, pill box, etc.);

a network input information input "NI" for receiving location information and activity levels in respect of other users of the network of systems relating to when those users have suffered an asthma attack; and an emergency input "Em" for receiving an indication from the user of an asthma attack.

When a user has an asthma attack, the emergency input Em is provided by the user. This may be a simple emergency button which is pressed by the user. This enables the system to associate the conditions at that time (location and activity level, and optionally also pollution levels or other allergen concentrations) with an asthma attack, so that other users with similar sensitivities to an attack can be warned, if they find themselves with the same set of conditions.

The outputs comprise:

an alert signal output "Alert" for warning the user of the risk of an asthma attack; and a network output information output "NO" for providing location information and activity levels to other users of the network of systems relating to when the user has suffered an asthma attack. The NO signal sent by the user corresponds to the NI signal received by other users with the network. The NI and NO information may also include an indication of the sensitivity of the user to the allergen present, or a general sensitivity level of the user.

The system may be divided into different parts in different ways. For example there are various sensors used, including a location sensor (such as a GSM signal processor for triangulation, or a GPS or other satellite positioning system), an activity sensor and (optionally) a heart rate sensor. There may be other sensors such as physiological sensors and also pollution sensors. These sensors may all be part of the system, or else some sensors may be part of other devices (with other primary functions) with which the system communicates.

In the example of FIG. 1, the system includes an activity monitor 12 such as an accelerometer or inertia sensor and a heart rate sensor 14. The other sensing functions are implemented by a mobile device (telephone or tablet) 16 with which the processor 10 communicates.

Thus, in this example, there is a set 18 of inputs/outputs for communication between the processor 10 and the mobile device 16. This may be a wireless link such as a Bluetooth connection. There is also a set 20 of wired connections. These include the emergency input Em which for example is a push button.

The interface to the network of systems as well as to other external data sources is implemented by the mobile device 16 in this example. It thus relays the external inputs NI and P to the system processor 10, and sends out the external output NO. However, this functionality may instead be implemented by units integrated into the system itself. The system may thus be a standalone system or else it may make use of other components.

Other physiological sensors may be used to assist in determining the activity level of the user. For example, devices for measuring the breathing effort (e.g. chest straps, acoustic detectors e.g. one or more microphones, flow sensors, etc.) can also be used instead of, or as well as, motion detectors.

The system thus tracks the physical activity level at a given time of the user, and at a particular location. The activity level is used to enable a total inhaled breath volume to be estimated. The breathing volume is for example generally proportional to the physical activity level.

Figures 2, 3, 4:
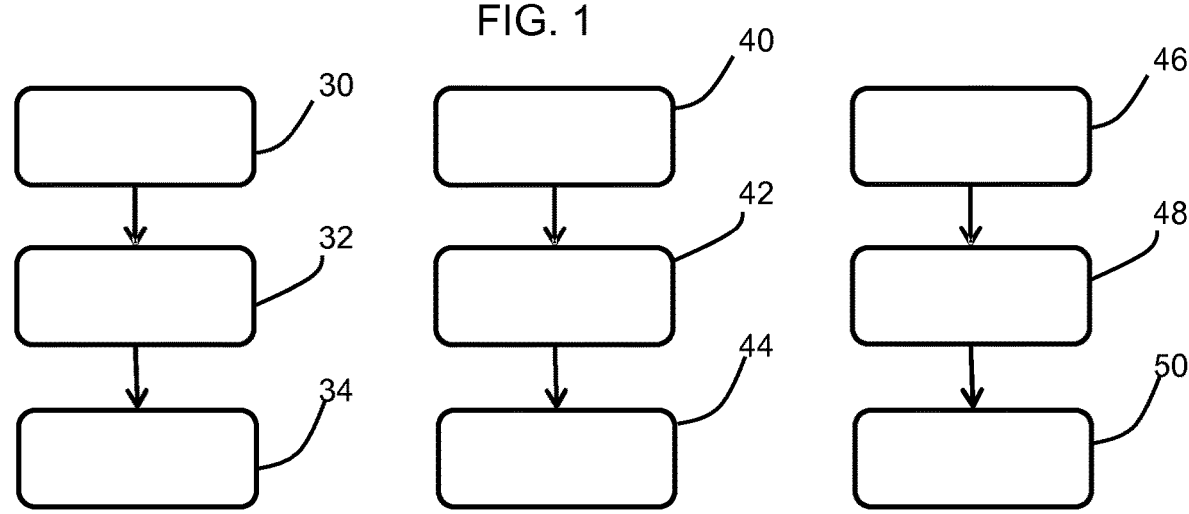
FIG. 2 shows a method of determining the total inhaled breath volume.
FIG. 3 shows a method of determining the concentration of asthma attack triggers.
FIG. 4 shows a method of determining the total amount of inhaled asthma triggers.

FIG. 2 shows a method of determining the total inhaled breath volume.

In step 30 the activity level information such as data from an inertia sensor, as well as any other physiological data such as heart rate, is monitored. Other parameters may also be used such as the body weight, age, and lung capacity of the user.

In step 32, the air volume per breath is calculated taking account of the data inputs from step 30.

In step 34, the total inhaled breath volume is estimated. This may be based on a time duration and the volume per breath. A breathing rate may be determined which itself takes account of the activity level, so that both the breathing rate and the breathing volume are estimated in dependence on the activity level. The breathing rate may instead be measured directly by a breathing counter (for example based on a microphone, inertia sensor, chest strap, etc.).

This information relates to the particular user.

The system also determines the concentration of asthma attack triggers (i.e. pollution levels) at a given location. This can be used to provide a risk factor in respect of specific locations at specific times.

FIG. 3 shows a method of determining the concentration of asthma attack triggers. In step 40, information is received from publicly available data sources. In step 42, the location of the user is determined and based on this, a risk factor can be determined in step 44 associated with the specific location of the user.

The publicly available information for example comprises databases of pollution information. In this way, the system does not need its own pollution sensing. However, the data may be supplemented by measurements made by the system from portable or wearable sensors. There may also be crowd sourced information from other users of the network of systems.

The publicly available information relates only to outdoor generated triggers.

The concentration of indoor triggers may also be taken into account. This can be based on indoor air quality monitoring using indoor air quality sensors and air management devices such as air purifiers. These sensors may be parts of other systems with which the system can communicate.

The system then determines the total amount of inhaled asthma triggers using the method shown in FIG. 4.

In step 46, the location-specific concentration of outdoor triggers is obtained from the method of FIG. 3. In step 48, the concentration of indoor triggers is obtained, if such information is relevant or available.

In step 50, the total inhaled trigger amount is obtained. This is based on the total inhaled breath volume from the method of FIG. 2 (and also based on the time spent the location) combined with the combined concentration of asthma triggers.

Gas sensors for detecting gases that are known to trigger asthma attacks, such as ozone and NO2, may be employed as a part of the system to be worn or carried by the user, for use at outdoor locations. However, as explained above, it is preferred to use publicly available data wherever available. For example, the ozone concentration at a given location is directly linked to the meteorological conditions (e.g., UV intensity, cloud coverage and wind) and form part of the weather forecast for a large portion of the world. In a similar approach, the NO2 concentration is closely linked to the traffic density, hence can also be predicted from the local traffic intensity, as an alternative of using dedicated sensors.

As a result of the difficulty of implementing wearable or portable pollen sensors, publicly available pollen risk maps may also be used instead of using local sensing.

The warning to be generated for a particular user takes account of user-specific information relating to the asthma triggers. This information includes, but is not limited to, the severity of the asthma of the user, information about the previous asthma attacks (e.g. the time, location, associated activity level, severity/intensity of the attack, the trigger, etc.) and the sensitivity to allergens, which can be compiled based on the users' experiences and/or by dedicated allergic reaction tests. Such allergy tests are well known.

In a most simple implementation, all users may be assumed to have the same asthma conditions, in which case there is no need to classify users, and the system will only be effective for one group of users. However, it is preferred that the system processes the data grouped per class of users, in terms of risk sensitivity. This information is provided by the user or a medical caregiver as an input (the input "S" in FIG. 1) based on their allergies and trigger sensitivities and prior attack history.

Each class is thus made up of users that have similar profiles in terms of the allergens that affect them and their sensitivities.

There may be different classes for different allergens or for different general sensitivities or both. The more classes that are defined, the more accurate the warning indication can be made, but there will be a smaller quantity of other user data relevant to a particular user.

One possible sensitivity classification is based on the trigger types in combination with the response level; for example 'grass—hypersensitive', 'birch—low sensitivity', etc. The number of classes may organically increase as the number of networked participants grows larger over time. There are several possible learning steps and implementation details:

1. All users indicate their sensitivities as they learn more about their condition.
2. Classes are formed for a minimum number of participants for a given location (e.g. at city level).
3. The minimum number of people in one class may be defined dynamically, for example proportional to the group population at the location level.

In this way, the system starts with a limited number of predefined classes (e.g. pollen, ozone, NO) and expands them by incorporating the sensitivity levels (for example low, medium and high) and further grows with increasing granularity for triggers (e.g. pollen type), and the sensitivity levels (low-mild-medium-active-high) as the number of networked users grows.

Moreover, the number of classes in use could be linked to the current number of users. If there are only a few users, the classification could be more general; if there are a large number of users, the classification could be better tailored to the trigger types and response levels, by increasing the granularity of the data when possible.

Figure 5:
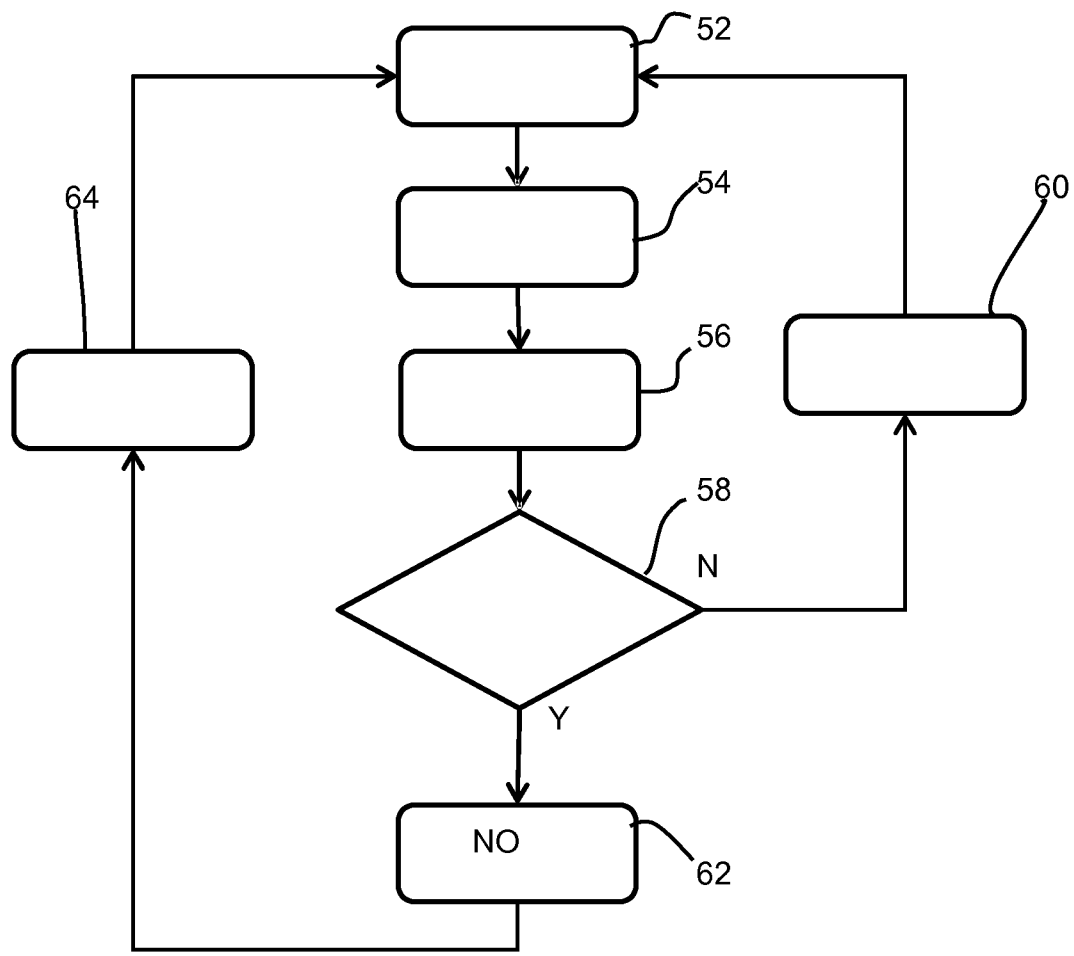
FIG. 5 shows a process for combining asthma attack information for a user in a particular class.

Once the user classes are defined, the process for combining the asthma attack information for a user in a particular class is shown in FIG. 5.

The process starts in step 52.

In step 54, the total inhaled trigger amount is derived in the manner explained above. This takes account of the activity level and thus provides normalization with respect to activity level.

In step 56, this inhaled trigger amount is normalized with regard to the sensitivity information.

In step 58, it is determined if the user has suffered an attack, based on an asthma attack indication, given by the user by pressing the emergency button. Alternatively, usage of a medication dispenser such as an inhaler which communicates with the system can also be used as input for capturing asthma attack events.

If there is no attack, there is no further action and the process returns to the start after a delay 60. Thus the monitoring process is performed periodically.

If there has been an attack, the information about the attack is provided to other users in step 62, and the network output information NO. This includes the characteristics of the user (which may simply be defined as the particular class for the user), the location, and the activity level. The activity level may be conveyed as the activity information itself, or the total inhaled breath volume (since the two are related).

The process then returns to the start after a delay 64.

The attack information, combined with the location and information regarding the user's identity (and the medical record) can be communicated to caregivers as well for timely intervention to the sufferer.

Figure 6:
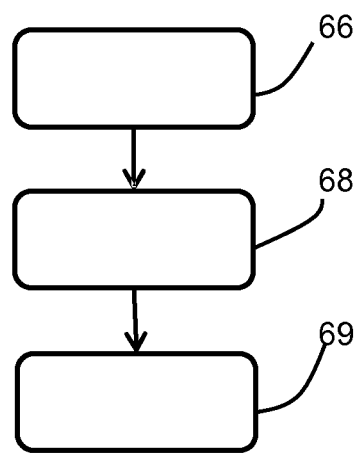
FIG. 6 shows a process for generating a warning for a user.

FIG. 6 shows how a warning is given to a user in advance of a likely attack.

In step 66, the activity level of the user, or the scheduled activity level is determined.

In step 68, the information received from the network of users is assessed to identify that other users in the same class (and therefore the same sensitivity) as the user have suffered attacks at similar activity levels (or activity levels planned by the user) and at the same location.

In step 69, a warning is provided if needed that the user should maintain a low activity level and/or take medicine. No warning is needed if the activity level is already sufficiently low.

It can be seen that by making warnings based on the experiences of other users, taking into primary account their activity levels and locations, there is no need to know any absolute air quality information. Air quality information may be used as well, either collected locally or from database sources, but this information is not needed for the system to be able to provide an effective warning.

The system thus simplifies the need for complex trigger measurements for asthma or other respiratory tract conditions. Instead of performing cumbersome analysis, activity levels of multiple users are tracked at a given location and at a given time frame. As soon as user, for example a user with the highest activity level, experience a problem the system issues a warning to all others who are still at a lower activity level. The activity based approach is not an add-on to air quality measurements, but instead the activity level functions as the primary source of information.

The wireless networking of the systems to form the network can be implemented using standard approaches which well-known. Technology possibilities include various short range communication systems for communication between different parts of the system (e.g. Bluetooth, Zigbee, etc.), and the GSM network (e.g. 3G or 4G) for the large area network for covering the outdoor operations. Although GSM networks are capable of providing location at a certain level of accuracy, further details can also be achieved by using various global positioning systems that are known in the field.

The invention is of interest for asthma patient monitoring systems, public health management systems, allergy management systems, air quality monitoring networks, and respiratory track conditions management.

The system described above makes use of a processor 10 for processing data.

Figure 7:
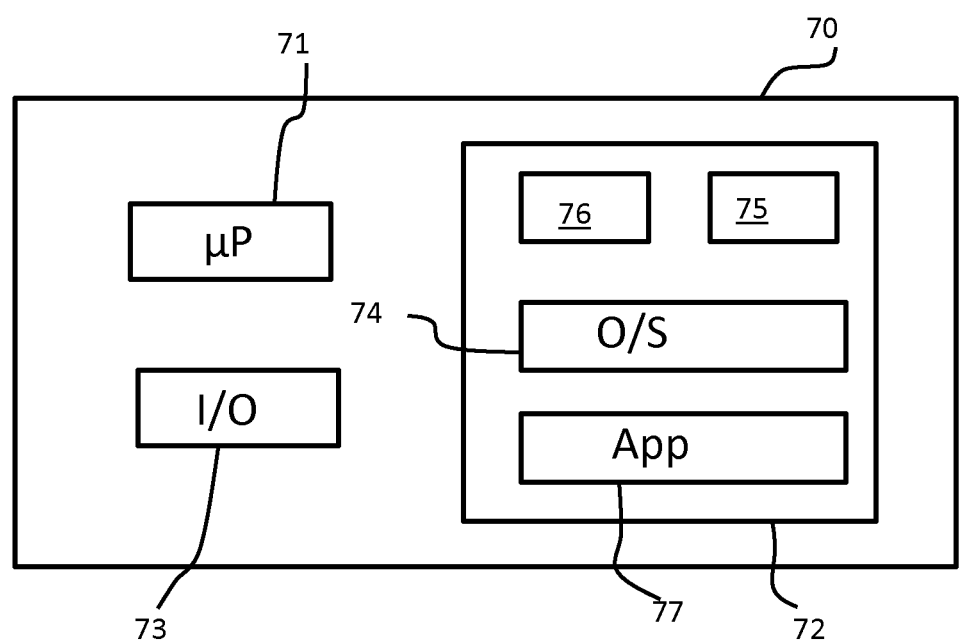
FIG. 7 illustrates an example of a computer for implementing the processor.

FIG. 7 illustrates an example of a computer 70 for implementing the processor described above.

The computer 70 includes, but is not limited to, PCs, workstations, laptops, PDAs, palm devices, servers, storages, and the like. Generally, in terms of hardware architecture, the computer 70 may include one or more processors 71, memory 72, and one or more I/O devices 73 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 71 is a hardware device for executing software that can be stored in the memory 72. The processor 71 can be virtually any custom made or commercially available processor, a central processing unit (CPU), a digital signal processor (DSP), or an auxiliary processor among several processors associated with the computer 70, and the processor 71 may be a semiconductor based microprocessor (in the form of a microchip) or a microprocessor.

The memory 72 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 72 may incorporate electronic, magnetic, optical, and/or other types of storage media. Note that the memory 72 can have a distributed architecture, where various components are situated remote from one another, but can be accessed by the processor 71.

The software in the memory 72 may include one or more separate programs, each of which comprises an ordered listing of executable instructions for implementing logical functions. The software in the memory 72 includes a suitable operating system (O/S) 74, compiler 75, source code 76, and one or more applications 77 in accordance with exemplary embodiments.

The application 77 comprises numerous functional components such as computational units, logic, functional units, processes, operations, virtual entities, and/or modules.

The operating system 74 controls the execution of computer programs, and provides scheduling, input-output control, file and data management, memory management, and communication control and related services.

Application 77 may be a source program, executable program (object code), script, or any other entity comprising a set of instructions to be performed. When a source program, then the program is usually translated via a compiler (such as the compiler 75), assembler, interpreter, or the like, which may or may not be included within the memory 72, so as to operate properly in connection with the operating system 74. Furthermore, the application 77 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 73 may include input devices such as, for example but not limited to, a mouse, keyboard, scanner, microphone, camera, etc. Furthermore, the I/O devices 73 may also include output devices, for example but not limited to a printer, display, etc. Finally, the I/O devices 73 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 73 also include components for communicating over various networks, such as the Internet or intranet.

When the computer 70 is in operation, the processor 71 is configured to execute software stored within the memory 72, to communicate data to and from the memory 72, and to generally control operations of the computer 70 pursuant to the software. The application 77 and the operating system 74 are read, in whole or in part, by the processor 71, perhaps buffered within the processor 71, and then executed.

When the application 77 is implemented in software it should be noted that the application 77 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A system for determining a risk level of a respiratory attack of a user of the system, wherein the system comprises part of a network of systems, the system comprising:
   an input arranged to receive information of a physical activity level or a planned physical activity level (Ac) of the user;
   an input arranged to receive location information (Loc) of the user;
   an input arranged to receive an indication (Em) from the user of a respiratory attack;
   an input arranged to receive location information and activity levels (NI) in respect of other users of the network of systems relating to when they have suffered a respiratory attack;
   an output arranged to report location information and activity level information (NO) of the user to other users of the network of systems relating to when the user has suffered a respiratory attack; and
   a user interface arranged to provide a warning to the user which takes account of the location of the user and the activity level or planned activity level of the user and the received location information and activity levels in respect of other users, wherein the user interface is adapted to provide a warning to the user only if their location and physical activity level or planned physical activity level is comparable to, or higher than, another user that suffered a respiratory attack.

2. A system as claimed in claim 1, further comprising an activity monitoring device for providing the physical activity level and wherein the activity monitoring device comprises an inertia sensor.

3. A system as claimed in claim 1, comprising a processor which is adapted to estimate an air volume per breath based on the activity level and on a default air volume per breath for the user.

4. A system as claimed in claim 3, wherein the processor is adapted to derive a trigger amount based on an estimated total breathed air volume.

5. A system as claimed in claim 4, further comprising a breathing counter, wherein the breathing counter information (BC) is used for estimating the total breathed air volume.

6. A system as claimed in claim 1, comprising an external input (P) for receiving information about pollution or allergen concentrations at the location of the user.

7. A system as claimed in claim 1, comprising an input (S) for receiving information relating to the sensitivity of the user to particular triggers, and wherein the warning takes account of the sensitivity information.

8. A system as claimed in claim 1, wherein the input for receiving an indication from the user of a respiratory attack comprises an emergency button.

9. A system as claimed in claim 1, having no local pollution sensing apparatus, or further comprising a pollution sensor for supplementing the generation of the warning.

10. A method for determining a risk level of a respiratory attack of a user who uses a risk assessment system, wherein the system comprises part of a network of systems, the method comprising:
    tracking the physical activity level of the user or determining a planned physical activity level for a user;
    receiving an indication from the user if and when they suffer a respiratory attack;
    receiving location information and activity levels in respect of other users of the network of systems, relating to when they have suffered a respiratory attack;
    reporting location information and activity level information of the user to other users of the network of systems, relating to when the user has suffered a respiratory attack; and
    providing a warning to the user which takes account of the location of the user and the activity level or planned activity level of the user and the received location information and activity levels in respect of other users, wherein a warning is provided to the user only if their location and physical activity level or planned physical activity level is comparable to, or higher than, another user that suffered a respiratory attack.

11. A method as claimed in claim 10, comprising estimating an air volume per breath based on the activity level and on a default air volume per breath for the user.

12. A method as claimed in claim 11, comprising deriving a trigger amount based on an estimated total breathed air volume.

13. A method as claimed in claim 10, comprising receiving information about pollution or allergen concentrations at the location of the user.

14. A method as claimed in claim 10, comprising generating the warning taking account of the sensitivity of the user to particular triggers.

15. A computer program comprising computer program code means which is adapted, when said program is run on a computer, to implement the method of claim 10.

* * * * *